(12) United States Patent
Kelly et al.

(10) Patent No.: US 12,329,563 B2
(45) Date of Patent: Jun. 17, 2025

(54) SYSTEM AND METHOD FOR CONTINUOUS CALIBRATION OF X-RAY SCANS

(71) Applicant: HOLOGIC, INC., Marlborough, MA (US)

(72) Inventors: Thomas Kelly, Woburn, MA (US); Kevin Wilson, Acton, MA (US); Mark Guetersloh, Bedford, MA (US); Wei Wang, Wellesley Hills, MA (US)

(73) Assignee: Hologic, Inc., Marlborough, MA (US)

( * ) Notice: Subject to any disclaimer, the term of this patent is extended or adjusted under 35 U.S.C. 154(b) by 345 days.

(21) Appl. No.: 17/612,476

(22) PCT Filed: May 20, 2020

(86) PCT No.: PCT/US2020/033783
§ 371 (c)(1),
(2) Date: Nov. 18, 2021

(87) PCT Pub. No.: WO2020/242855
PCT Pub. Date: Dec. 3, 2020

(65) Prior Publication Data
US 2022/0225957 A1    Jul. 21, 2022

Related U.S. Application Data

(60) Provisional application No. 62/853,379, filed on May 28, 2019.

(51) Int. Cl.
*A61B 6/00* (2024.01)
*A61B 6/02* (2006.01)
(Continued)

(52) U.S. Cl.
CPC .............. *A61B 6/583* (2013.01); *A61B 6/027* (2013.01); *A61B 6/06* (2013.01); *A61B 6/4035* (2013.01);
(Continued)

(58) Field of Classification Search
CPC .................................................. A61B 6/5258
See application file for complete search history.

(56) References Cited

U.S. PATENT DOCUMENTS

| | | |
|---|---|---|
| 4,811,373 A | 3/1989 | Stein |
| 4,831,527 A | 5/1989 | Clark |

(Continued)

FOREIGN PATENT DOCUMENTS

| | | |
|---|---|---|
| CN | 1767788 | 5/2006 |
| CN | 202723867 | 2/2013 |

(Continued)

OTHER PUBLICATIONS

European Extended Search Report in U.S. Appl. No. 20/814,137, mailed May 12, 2023, 5 pages.

(Continued)

*Primary Examiner* — Dani Fox
*Assistant Examiner* — Shun Lee
(74) *Attorney, Agent, or Firm* — Merchant & Gould P.C.

(57) ABSTRACT

A dual-energy X-ray absorptiometry ("DXA") system includes an x-ray source assembly comprising a source carriage to move the x-ray source assembly along a scan path, the scan path comprising an active scan portion and a reference measurement portion. A detector assembly including a detector carriage to move the detector assembly with the source assembly and to collect scan data at active scan portions. A support structure supporting the source and detector assemblies. A calibration controller coupled a calibration element having a known x-ray attenuation value and configured position the calibration element between the source and detector assemblies during the reference measurement portion and to remove the calibration element from between the source and detector assemblies during the active scan portion. A processing unit operable to compare the (Continued)

reference measurement against an expected reference value to identify a variance and to selectively trigger an action in response to the variance.

24 Claims, 8 Drawing Sheets

(51) Int. Cl.
  *A61B 6/06* (2006.01)
  *A61B 6/40* (2024.01)
  *A61B 6/58* (2024.01)
(52) U.S. Cl.
  CPC .......... *A61B 6/4071* (2013.01); *A61B 6/4078* (2013.01); *A61B 6/4085* (2013.01); *A61B 6/482* (2013.01); *A61B 6/5258* (2013.01); *A61B 6/54* (2013.01)

(56) References Cited

U.S. PATENT DOCUMENTS

| | | | |
|---|---|---|---|
| 4,947,414 A | 8/1990 | Stein | |
| 4,980,904 A | 12/1990 | Sones et al. | |
| 5,040,199 A * | 8/1991 | Stein | H05G 1/26 |
| | | | 378/146 |
| 5,305,368 A | 4/1994 | Bisek et al. | |
| 5,335,260 A * | 8/1994 | Arnold | A61B 6/583 |
| | | | 378/207 |
| 5,771,272 A | 6/1998 | Berger et al. | |
| 5,778,045 A * | 7/1998 | von Stetten | A61B 6/488 |
| | | | 378/98.9 |
| 5,949,846 A | 9/1999 | Stein et al. | |
| 6,081,582 A | 6/2000 | Mazess | |
| 6,102,567 A | 8/2000 | Cabral | |
| 6,160,866 A | 12/2000 | Mazess | |
| 6,173,034 B1 | 1/2001 | Chao | |
| 6,198,797 B1 | 3/2001 | Majima et al. | |
| 6,215,846 B1 | 4/2001 | Mazess | |
| 6,233,473 B1 | 5/2001 | Shepherd | |
| 6,315,447 B1 | 11/2001 | Nord | |
| 6,468,209 B1 | 10/2002 | Heymsfield | |
| 6,816,564 B2 | 11/2004 | Charles, Jr. | |
| 6,969,350 B1 | 11/2005 | Hawthorne | |
| 6,999,549 B2 | 2/2006 | Sabol et al. | |
| 7,198,404 B2 | 4/2007 | Navab et al. | |
| 7,444,961 B1 | 11/2008 | Ellis | |
| 7,595,043 B2 | 9/2009 | Hedrick | |
| 7,725,153 B2 | 5/2010 | Kelly et al. | |
| 7,801,350 B2 | 9/2010 | La Bras et al. | |
| 8,300,911 B1 | 10/2012 | Payne et al. | |
| 8,483,458 B2 | 7/2013 | Payne et al. | |
| 8,634,629 B2 | 1/2014 | Wilson | |
| 8,792,689 B2 | 7/2014 | Kelly et al. | |
| 9,086,356 B1 | 7/2015 | Kelly et al. | |
| 9,161,727 B2 | 10/2015 | Jenkins | |
| 9,179,873 B2 | 11/2015 | Kelly et al. | |
| 9,504,406 B2 | 11/2016 | Chetham et al. | |
| 9,642,585 B2 | 5/2017 | Wilson | |
| 9,865,050 B2 | 1/2018 | Kelly et al. | |
| 10,390,784 B2 | 8/2019 | Wilson | |
| 10,470,705 B2 | 11/2019 | Kelly | |
| 10,499,865 B2 | 12/2019 | Wilson et al. | |
| 10,515,451 B2 | 12/2019 | Kelly | |
| 10,646,159 B2 | 5/2020 | Kelly | |
| 10,966,678 B2 | 4/2021 | Wilson | |
| 11,058,380 B2 | 7/2021 | Wilson | |
| 11,625,824 B2 | 4/2023 | Kelly | |
| 11,701,079 B2 | 7/2023 | Wilson | |
| 11,717,244 B2 | 8/2023 | Wilson | |
| 2001/0053202 A1 | 12/2001 | Mazess | |
| 2002/0070365 A1 | 6/2002 | Karellas | |
| 2004/0077088 A1 | 4/2004 | Charles, Jr. et al. | |
| 2004/0101086 A1 | 5/2004 | Sabol et al. | |
| 2004/0247076 A1 | 12/2004 | Navab et al. | |
| 2005/0010106 A1 | 1/2005 | Lang et al. | |
| 2005/0215882 A1 | 9/2005 | Chenevert | |

| | | |
|---|---|---|
| 2006/0074288 A1 | 4/2006 | Kelly et al. |
| 2007/0223795 A1 | 9/2007 | Qing et al. |
| 2007/0238957 A1 | 10/2007 | Yared |
| 2009/0279672 A1 | 11/2009 | Reiner |
| 2010/0081960 A1 | 4/2010 | McKenna |
| 2010/0086185 A1 | 4/2010 | Weiss |
| 2010/0168530 A1 | 7/2010 | Chetham |
| 2010/0168551 A1 | 7/2010 | Moller |
| 2010/0234719 A1 | 9/2010 | Kelly et al. |
| 2011/0002522 A1 | 1/2011 | Goto |
| 2011/0058725 A1 | 3/2011 | Markwardt et al. |
| 2011/0158386 A1 | 6/2011 | Payne et al. |
| 2011/0164798 A1 | 7/2011 | Masumoto |
| 2011/0235886 A1 | 9/2011 | Kelly et al. |
| 2011/0311122 A1 | 12/2011 | Kelly |
| 2012/0004570 A1 | 1/2012 | Shimizu |
| 2013/0051523 A1 | 2/2013 | Davydov et al. |
| 2013/0121461 A1 | 5/2013 | Toll |
| 2013/0308752 A1 | 11/2013 | Wilson |
| 2014/0288420 A1 | 9/2014 | Goossen et al. |
| 2014/0371570 A1 | 12/2014 | Davis et al. |
| 2015/0036910 A1 | 2/2015 | Kelly et al. |
| 2015/0146851 A1 | 5/2015 | Wilson |
| 2015/0374291 A1 | 12/2015 | Kelly et al. |
| 2016/0228057 A1 | 8/2016 | Kelly et al. |
| 2017/0046837 A1 | 2/2017 | Leinhard et al. |
| 2017/0135655 A1 | 5/2017 | Wang et al. |
| 2018/0021001 A1 | 1/2018 | Wilson |
| 2018/0049710 A1 | 2/2018 | Wilson |
| 2018/0189948 A1 | 7/2018 | Kelly |
| 2019/0059829 A1 | 2/2019 | Han |
| 2019/0102877 A1 | 4/2019 | Payne et al. |
| 2020/0029927 A1 | 1/2020 | Wilson |
| 2020/0046307 A1 | 2/2020 | Wilson |
| 2020/0060636 A1 | 2/2020 | Wilson |
| 2020/0167921 A1 | 5/2020 | Kelly |
| 2021/0052243 A1 | 2/2021 | Don et al. |
| 2021/0150704 A1 | 5/2021 | Bruening et al. |
| 2021/0177368 A1 | 6/2021 | Wilson |
| 2021/0361251 A1 | 11/2021 | Wilson |
| 2023/0306594 A1 | 9/2023 | Kelly |
| 2023/0404507 A1 | 12/2023 | Wilson |

FOREIGN PATENT DOCUMENTS

| | | |
|---|---|---|
| DE | 10 2012 204429 A1 | 9/2013 |
| EP | 0747008 A1 | 12/1996 |
| EP | 1882447 | 1/2008 |
| JP | H04-263842 | 9/1992 |
| JP | H09108206 A | 4/1997 |
| JP | H10-151127 | 6/1998 |
| JP | 2004-081394 | 3/2004 |
| JP | 2007-524438 | 8/2007 |
| JP | 2010-042129 | 2/2010 |
| JP | 2010-57953 | 3/2010 |
| JP | 2010-510835 | 4/2010 |
| JP | 2010-253049 | 11/2010 |
| JP | 2010-253106 | 11/2010 |
| JP | 2011024773 | 2/2011 |
| JP | 2013-516706 | 5/2013 |
| JP | 6047347 B2 | 12/2016 |
| JP | 2018506385 | 3/2018 |
| KR | 2018-0038251 | 4/2018 |
| WO | 2003052398 A1 | 6/2003 |
| WO | 2010/051600 | 5/2010 |
| WO | 2010/095709 | 8/2012 |
| WO | 2014/066906 | 5/2014 |
| WO | 2016/138262 | 9/2016 |
| WO | 2016/177798 | 11/2016 |
| WO | 2017/055352 | 4/2017 |
| WO | 2018192909 A1 | 10/2018 |
| WO | 2022/139874 | 6/2022 |

OTHER PUBLICATIONS

International Search Report and Written Opinion for International application No. PCT/US2020/033783, mailed Sep. 9, 2020, 11 pages.

(56) References Cited

OTHER PUBLICATIONS

Stein et al., "A Duel-Energy X.Ray Bone Densitometer incorporating an internal reference system", Workshop on Non-Invasive Bone Measurements, Leuven, Belgium, Sep. 1987.
Author Unknown., "National Health and Nutrition Examination Survey (NHANES): Dual Energy Xray Absorptiometry (DXA) Procedures Manual", CDC, Jan. 2017.
PCT International Preliminary Report on Patentability in Application PCT/US2020/033783, mailed Dec. 9, 2021, 8 pages.
Bertin et al., "Measurement of visceral adipose tissue by DXA combined with anthropometry in obese humans," Int J Obes Relat Metab Disord., 24(3):263-270 (Mar. 2000).
Chan, "Performance of Dual-Energy X-ray Absorptiometry in Evaluating Bone, Lean Body Mass, and Fat in Pediatric Subjects", Journal of Bone and Mineral Research, vol. 7 (Year 1992), 7 pgs.
Chan-Shien, Ho, et al., "Application of deep learning neural network in predicting bone mineral density from plain X-ray radiography", Archives of Osteoporosis, Springer, London, vol. 16, No. 1, Oct. 9, 2021, 12 pages.
De Lorenzo, A. et al., "Predicting body cell mass with bioimpedance by using theoretical methods: a technological review", J. Appl. Physiol 1997; 82: 1542-58.
De Souza, Joao et al., "Predicting body measures from 2D images using Convolutional Neural Networks", 2020 International Joint Conference on Neural Networks (IJCNN), IEEE, Jul. 19, 2020, pp. 1-6.
Gronenmeyer et al., "Fast Adipose Tissue (FAT) Assessment by MRI," Magnetic Resonance Imaging, 18:815-818 (2000).
Hayashi et al., "Visceral Adiposity and the Prevalence of Hypertension in Japanese Americans," Circulation, 108:1718-1723 (2003).
Hill et al., "Estimating Abdominal Adipose Tissue With DXA and Anthropometry," Obesity, 15(2):504-510 (Feb. 2007).
Hologic Clarity of Vision, Discovery QDR Series Advanced Point-of-Care Bone Health Assessment, Hologic Osteoporosis Assessment (May 2004), 13 pages.
Hologic Clarity of Vision, Explorer Fan-Beam DXA for the Cost-Conscious Practice, Hologic Osteoporosis Assessment (Jan. 2004), 11 pages.
Jensen et al., "Measurement of abdominal and visceral fat with computed tomography and dual-energy x-ray absorptiometry," Am J Clin Nutr., 61(2):274-278 (Feb. 1995).
Kamel et al., "Usefulness of Anthropometry and DXA in Predicting Intra-abdominal Fat in Obese Men and Women," Obesity Research, 8(1) 36-42 (2000).
Kelly et al., "DXA Body Composition: Theory and Practice," Appl Radia., 49(5:6):511-513 (1988).
Kobayashi et al., "A novel method of measuring intra-abdominal fat volume using helical computed tomography," International Journal of Obesity, 26:398-402 (2002).
Krotkiewski et al., "Impact of Obesity on Metabolism in Men and Women. Importance of Regional Adipose Tissue Distribution," J Clin Invest., The American Society for Clinical Investigation, Inc., 72:1150-1162 (1983).
Kvist et al., "Total and visceral adipose-tissue volumes derived from measurements with computed tomography in adult men and women: predictive equations 1-3," Am J Clin Nutr, 48:1351-1361 (1988).
Lehmann et al., "Generalized Image Combinations in Dual KVP Digital Radiography", Med. Phys. 8(5) Sep./Oct. 1981, 9 pgs.
Ley, "Sex- and menopause-associated changes in body-fat distribution," Am J Clin Nut, 55:950-954 (1993).
Lustgarten, M.S. et al., "Assessment of Analytical Methods Used to Measure Changes in Body Composition in the Elderly and Recommendations for Their Use in Phase II Clinical Trials", J. Nutr. Health Aging, 15(5): 368-375 (2011).
Malkov, S. et al., "Combining 3D optical imaging and dual energy absorptiometry to measure three compositional components", Progress in Biomedical Optics and Imaging, SPIE—Int'l. Society for Optical Engineering, 8937: 893714-893714-6 (2014).

McKiernan F.E., et al. "A long femur scan field does not alter proximal femur bone mineral density measurements by dual-energy X-ray absorptiometry." J Clin Densitom. Jul.-Sep. 2011;14(3):354-8.
Miccini, Riccardo et al., "HRTF Individualization using Deep Learning", 2020 IEEE Conference on Virtual Reality and 3D User Interfaces Abstracts and Workshops (VRW), IEEE, Mar. 22, 2020, pp. 390-395.
Michael et al., "Monte Carlo modelling of an extended DXA technique", Physics in Medicine and Biology, vol. 43, No. 9, Sep. 1, 1998, pp. 2583-2596.
Montague et al., "Perspectives in Diabetes the Perils of Portliness Causes and Consequences of Visceral Adiposity," Diabetes, 49:883-888 (2000).
Morricone et al., "Relationship of Visceral Fat Distribution to Angiographically Assessed Coronary Artery Disease: Results in Subjects With or Without Diabetes or Impaired Glucose Tolerance," PMID: 12616807 [PubMed-indexed for Medline], Nutr Metab Cardiovasc Dis., 12(5):275-283 (2002).
Nicklas et al., "Visceral Adipose Tissue Cutoffs Associated With Metabolic Risk Factors for Coronary Heart Disease in Women," Epidemiology/Health Services/Psychosocial Research, Diabetes Care, 26:1413-1420 (May 2003).
Pietrobelli, A. et al., "Dual-energy X-ray absorptiometry: fat estimation errors due to variation in soft tissue hydration", The American Physiological Society, 1998, vol. 274(5), pp. E808-E816.
Prado, C. et al., "Lean Tissue Imaging: A New Era for Nutritional Assessment and Intervention", Journal of Parental and Enteral Nutrition, 38(8): 940-953 (2014).
Pritchard et al., "Evaluation of Dual Energy X-Ray Absorptiometry as a Method of Measurement of Body Fat," European Journal of Clinical Nutrition, 47:216-228 (1993).
Sanada et al., "A cross-sectional study of sarcopenia in Japanese men and women: Reference values and association with cardiovascular risk factors", European Journal of Applied Physiology 110(1): 57-65, Sep. 2010.
Sayer, A.A. et al., "New horizons in the pathogenesis, diagnosis and management of sarcopenia", Age and Ageing, 42: 145-150 (2013).
Shane, E., et al. "Atypical subtrochanteric and diaphyseal femoral fractures: report of a task force of the American Society for Bone and Mineral Research." J Bone Miner Res. Nov. 2010;25(11):2267-94.
Shane, E., et al."Atypical subtrochanteric and diaphyseal femoral fractures: Second report of a task force of the American society for bone and mineral research." J Bone Miner Res. May 28, 2013. doi: 10.1002/jbmr.1998. [Epub ahead of print], pp. 1-23.
Slosman et al., "Assessment of Whole-Body Composition With Dual-Energy X-Ray Absorptiometry," Radiology, 185:593-598 (1992).
Sorenson, J.A. et al., "Simulation of dual-energy x-ray absorptiometry", Medical Physics, 16(1): 75-80 (1989).
Tan et al., "Sarcopenia in an Overweight or Obese Patient is an Adverse Prognostic Factor in Pancreatic Cancer", Xlin Cancer Res 2009; 15(22), Nov. 15, 2009, pp. 6973-6979.
Trueth et al., "Estimating Intraabdominal Adipose Tissue in Women by Dual-Energy X-Ray Absorptiometry," Am J Clin Nutr, 62:427-432 (1995).
Wear, J. et al., "CZT detector for dual-energy x-ray absorptiometry (DEXA)", Proceedings of SPIE, 4142: 175-188 (2000).
WHO publication—Kanis JA, on behalf of the World Health Organisation Scientific Group, "Assessment of osteoporosis at the primary health care level", WHO Collaborating Centre for Metabolic Bone Diseases, University of Sheffield 2007, 339 pgs.
Wilson, J.P et al., "Improved 4-Compartment body-composition model for a clinically accessible measure of total body protein", Am J Clin Nutr. 2013; 97: 497-504.
Wilson, J.P. et al., "Dual-Energy X-Ray absorpitometry-based body volume measurement for 4-compartment body composition", The American Journal of Clinical Nutrition, 2012; 95 (1): 25-31.
Yamada, Yosuke, The appraisal method of Yosuke, and the amount of skeletal muscle and muscular power, medical development, Mar. 1, 2014, vol. 248, No. 9, pp. 670-678, with an English translation summary.

(56) References Cited

OTHER PUBLICATIONS

Zimmermann et al., "Detection of overweight and obesity in a national sample of 6-12 year old Swiss children: accuracy and validity of reference values for body mass index from the US Centers for Disease Control and Prevention and the International Obesity Task Force", 2010, Am J Clin Nutr 2004; 79; 838-43.

Hayes et al., "DXA: Potential for Creating a Metabolic Map of Organ-Tissue Resting Energy Expenditure Components", Obesity Research vol. 10, No. 10, Oct. 2002, pp. 969-977.

Ho, Chan-Shien et al., "Application of deep learning neural network in predicting bone mineral density from plain X-ray radiography", Archives of Osteoporosis, Springer London, vol. 16, No. 1, Oct. 9, 2021, 12 pgs.

Rafael do Espirit Santo, "Principal Component Analysis applied to Digital Image Compression", Einstein (Sao Paulo) 10 (2), Jun. 2012 (available at https://doi.ord/10.1590S1679-45082012000200004), pp. 135-139.

\* cited by examiner

SYSTEM AND METHOD FOR CONTINUOUS CALIBRATION OF X-RAY SCANS

CROSS-REFERENCE TO RELATED APPLICATIONS

This application is a 371 of International Patent Application No. PCT/US2020/033783, filed May 20, 2020, which claims the benefit of U.S. Provisional Patent Application No. 62/853,379, filed May 28, 2019. The subject matter of the aforementioned international and U.S. provisional patent applications are hereby incorporated herein by reference in their respective entireties for all purposes.

BACKGROUND

Dual-energy X-ray absorptiometry ("DXA" or "DEXA") is a low-dose imaging technology used to measure body characteristics including bone mineral density (BMD) and bone mineral content (BMC). All DXA systems make use of the differential attenuation of the X-ray beam at two energies to calculate the bone mineral content and soft tissue composition in the scanned region. Most DXA instruments measure bone mineral density in the clinically important sites of the spine, hip, and forearm. DXA scan results are often used to diagnose and follow osteoporosis over time. The accuracy and reliability of BMD measurements are important to detect changes in patient bone loss. To maintain measurement precision and accuracy, DXA systems are calibrated to predetermined performance standards using defined quality control ("QC") test procedures.

A typical QC testing includes positioning a phantom device in the DXA system and obtaining a DXA scan of the phantom device. The obtained DXA scan may be compared to a previously calibrated DXA scan of the phantom to expose variations in system performance between the successive scans.

SUMMARY

The QC testing technique discussed above is generally performed on a periodic (daily, weekly) basis, and therefore may fail to capture interim drifts in system performance Drifts in system performance, for example caused by x-ray system component issues or x-ray detector instability, may diminish the accuracy and precision of BMD and BMC results. Diminished accuracy and precision may lead to misdiagnosis or delay proper patient diagnosis and treatment, or result in DXA scan results being discarded, in which case the patient may need to be rescanned, thereby inconveniencing the patient and reducing the overall efficiency and efficacy of the DXA procedure.

According to one aspect it is realized that the problems of delayed diagnosis, customer inconvenience and discarded DXA scans may be overcome through the introduction of a system that continually monitors QC reference measurements to detect DXA performance deviations in real-time. Detecting performance deviations in real-time enables real time (or near real-time) DXA scan data correction, thereby improving diagnostic accuracy, expediting treatment plans, and reducing patient inconvenience and callbacks.

In one embodiment an x-ray system is disclosed. The X-ray system comprising an x-ray source assembly comprising a source carriage configured to move the x-ray source assembly along a scan path during a scan of the x-ray system, the scan path comprising an active scan portion and a reference measurement portion. The x-ray system further includes an x-ray detector assembly including a detector carriage configured to move the x-ray detector assembly synchronously with the x-ray source assembly along the scan path and to collect scan data at active scan portions of the scan path. The x-ray system may further include a support structure (e.g., c-shaped support structure) including a first end supporting the x-ray source assembly and a second end supporting the x-ray detector assembly. In one embodiment, the x-ray system includes a calibration element comprising a material having a known x-ray attenuation value and a calibration controller coupled to the calibration element and configured to position the calibration element between the x-ray source assembly and the x-ray detector assembly during the reference measurement portion of the scan path and to remove the calibration element from between the x-ray source assembly and the x-ray detector assembly during the active scan portion of the scan path. The x-ray system may also include a processing unit operable to compare the reference measurement against an expected reference value to identify a variance and to selectively trigger an action (e.g., a corrective action) in response to the variance.

In some embodiments, the active scan portion of the scan path comprises scan path locations that are aligned with an active scan area of the x-ray system. In some embodiments, the x-ray system includes an available scan area corresponding to a mechanical extent of travel of the x-ray source and x-ray detector, and wherein the reference measurement portion of the scan path includes at least one scan path location that is within the available scan area but outside the active scan area. In some embodiments, the reference measurement portion comprises a plurality of reference measurement locations within the scan path that are within the available scan area but outside the active scan area. In some embodiments, at least one reference measurement location in the reference portion of the scan path may be associated with a scan path location that is aligned with a low attenuation patient feature. In some embodiments, the low attenuation patient feature includes one or more of a patient soft tissue mass and a patient boundary.

In some embodiments, selective triggering of the action occurs in response to the variance exceeding a predetermined threshold range. In some embodiments, a type of action may be determined according to a degree by which the variance exceeds the predetermined threshold range. In some embodiments, selective triggering of action may be forestalled if a predetermined percentage of a plurality of reference measurements obtained during the reference portion of the scan path are below the predetermined threshold range. In some embodiments, the action may include one or more of a scan modification action and a system adjustment action.

In some embodiments, the scan modification action includes an adjustment of the scan data by an amount to normalize the variance using a plurality of variances associated with the plurality of reference measurements. In some embodiments, the amount may be determined based on one of a mean or a median of the plurality of variances. In some embodiments, the action may apply the amount to retrospective and prospective scan data. In some embodiments, the scan modification action includes performing a new scan to produce updated scan data. In some embodiments, the system modification action may include a system shutdown, system restart and field service notification. In some embodiments, the calibration element may be comprised of a bone equivalent material. In some embodiments, the bone equivalent material comprises one or more of bone, aluminum, a calcium phosphate compound, or some other combination of materials having x-ray attenuation characteristics similar to human bone. In some embodiments, the DXA system (e.g., the calibration controller) includes an advancement mechanism for moving the calibration element into an x-ray beam path between the x-ray source and x-ray detector during the reference measurement portion of the scan path. In some embodiments, the advancement mechanism may comprise, for example, a solenoid plunger. In some embodiments, the advancement mechanism may slide the calibration element into the x-ray beam path. In some embodiments, the advancement mechanism may rotate the calibration element into the x-ray beam path. In some embodiments, the x-ray source may emit an x-ray beam having a profile comprising one of a pencil beam, a thin fan beam, a narrow angle fan beam, a wide-angle fan beam, or a cone beam. In some embodiments, the x-ray source assembly further includes a filter, positioned in front of a collimator, the filter comprising a rare-earth x-ray filtration material. In some embodiments, the scan path is a boustrophedon pattern.

In another embodiment, the desired field of view is measured in a single exposure or alternating high and low energy exposures but without scanning motion, using an area detector, for example using a digital flat panel detector as in general radiography. In this embodiment the bone calibration element may be placed in the periphery of the field of view, outside of the bony region of interest, e.g. as a linear strip or mask of calibration material conforming to the soft tissue region at the periphery of the bone region under interrogation. The signal from calibration element is compared to previously determined threshold values; if it is outside a specified range the exam is flagged for corrective action including one or more of a scan modification action and a system adjustment or calibration action.

In another embodiment, a method of calibrating an x-ray system is disclosed. The method includes the steps of moving an x-ray source and x-ray detector pair synchronously along a defined scan path during an x-ray scan of a patient positioned between the x-ray source and x-ray detector pair, wherein the defined scan path comprises an active scan portion and a reference measurement portion. The method includes acquiring scan data while the x-ray source and x-ray detector pair advance along the active scan portion of the scan path and acquiring reference measurements when the x-ray source and x-ray detector pair advance along the reference measurement portion of the scan path including moving a calibration element between the x-ray source and x-ray detector pair during the reference measurement portion of the scan path. The method includes imaging the calibration element to generate the reference measurement and removing the calibration element from between the x-ray source and detector pair following the reference measurement. The method includes the steps of analyzing the reference measurement to identify a variance and selectively triggering a corrective action in response to the identified variance.

In one embodiment, the active scan portion of the scan path comprises scan path locations that are aligned with an active scan area of the x-ray system. In one embodiment, the x-ray system may comprise an available scan area corresponding to a mechanical extent of travel of the x-ray source and x-ray detector, and wherein the reference measurement portion of the scan path includes at least one scan path location that is within the available scan area but outside the active scan area. In one embodiment, the reference measurement portion may comprise a plurality of reference measurement locations within the scan path that are within the available scan area but outside the active scan area. In one embodiment, at least one reference measurement location in the reference portion of the scan path may be associated with a scan path location that is aligned with a low attenuation patient feature. In one embodiment, the low attenuation patient feature may include one or more of a patient soft tissue mass and a patient boundary. In one embodiment, the step of selective triggering of the action may occur in response to the variance exceeding a predetermined threshold range. In one embodiment, a type of action may be determined according to a degree by which the variance exceeds the predetermined threshold range. In one embodiment, the step of selectively triggering the action may be forestalled if a predetermined percentage of a plurality of reference measurements obtained during the reference portion of the scan path are below the predetermined threshold range. In one embodiment, the step of selectively triggering the action may include the steps of modifying the scan data and executing a procedure by the x-ray system. In one embodiment, the step of modifying the scan data may include adjusting the scan data by an amount to normalize the variance using a plurality of variances associated with a plurality of reference measurements. In some embodiments, the amount may be determined based on one of a mean or a median of the plurality of variances. In one embodiment, the step of modifying the scan data may include adjusting at least one of retrospective and prospective scan data. In one embodiment, the step of modifying the scan data may include performing a new scan to produce updated scan data. In one embodiment, the step of executing a procedure by the x-ray system may include one or more of performing a system shutdown, performing a system restart and notifying field service.

In some embodiments, the calibration element is comprised of a bone equivalent material. In one embodiment, the bone equivalent material may comprise one or more of bone, aluminum, a calcium phosphate compound, or other combinations of materials having x-ray attenuation properties similar to human bone.

In some embodiments, the step of moving the calibration element between the x-ray source and x-ray detector includes one of sliding the calibration element and rotating the calibration element. In one embodiment, the scan path may travel a boustrophedon pattern.

In another embodiment, a dual-energy X-ray absorptiometry (DXA) system is disclosed. The DXA system includes: an x-ray source and detector pair, configured to move along a scan path during a DXA scan and to acquire DXA scan data when the x-ray source and detector pair are within an active scan portion of the scan path, wherein the active scan portion of the scan path corresponds to scan path locations aligned with an active scan area of the DXA system. The DXA system is further configured to acquire a plurality of reference measurements when the x-ray source and detector pair are outside of an active scan area portion of the scan path. The DXA system includes a calibration controller comprising a calibration element coupled to the x-ray source and moveably configured to attenuate the x-ray signal during the plurality of reference measurements of the scan; and a processing unit operable to compare the plurality of reference measurements against an expected reference value to identify variances associated with system performance issues and to selectively initiate a corrective action to modify the DXA scan data in response to the identified variances.

In another embodiment, a method of calibrating a dual-energy X-ray Absorptiometry (DXA) system having an available scan area and an active scan area is disclosed. The method includes the steps of collecting DXA scan data by an x-ray source and x-ray detector pair when the x-ray source and x-ray detector pair are within the active scan area of the DXA system, collecting quality control reference measurements when the x-ray source and x-ray detector pair are outside the active scan area but within the available scan area and analyzing the quality control reference measurements to identify variances between the quality control reference measurements and an expected measurement. The method includes selectively modifying the DXA scan data in response to the identified variances, including foregoing modification of the DXA scan data if a minimum number of the quality control reference measurements are within a predetermined threshold range.

Such an arrangement, which continuously captures quality control reference measurements facilitates real-time DXA scan adjustments to compensate for drifts in system performance. These and other features will now be described in more detail below with regards to the attached figures.

DETAILED DESCRIPTION

Figure 1:
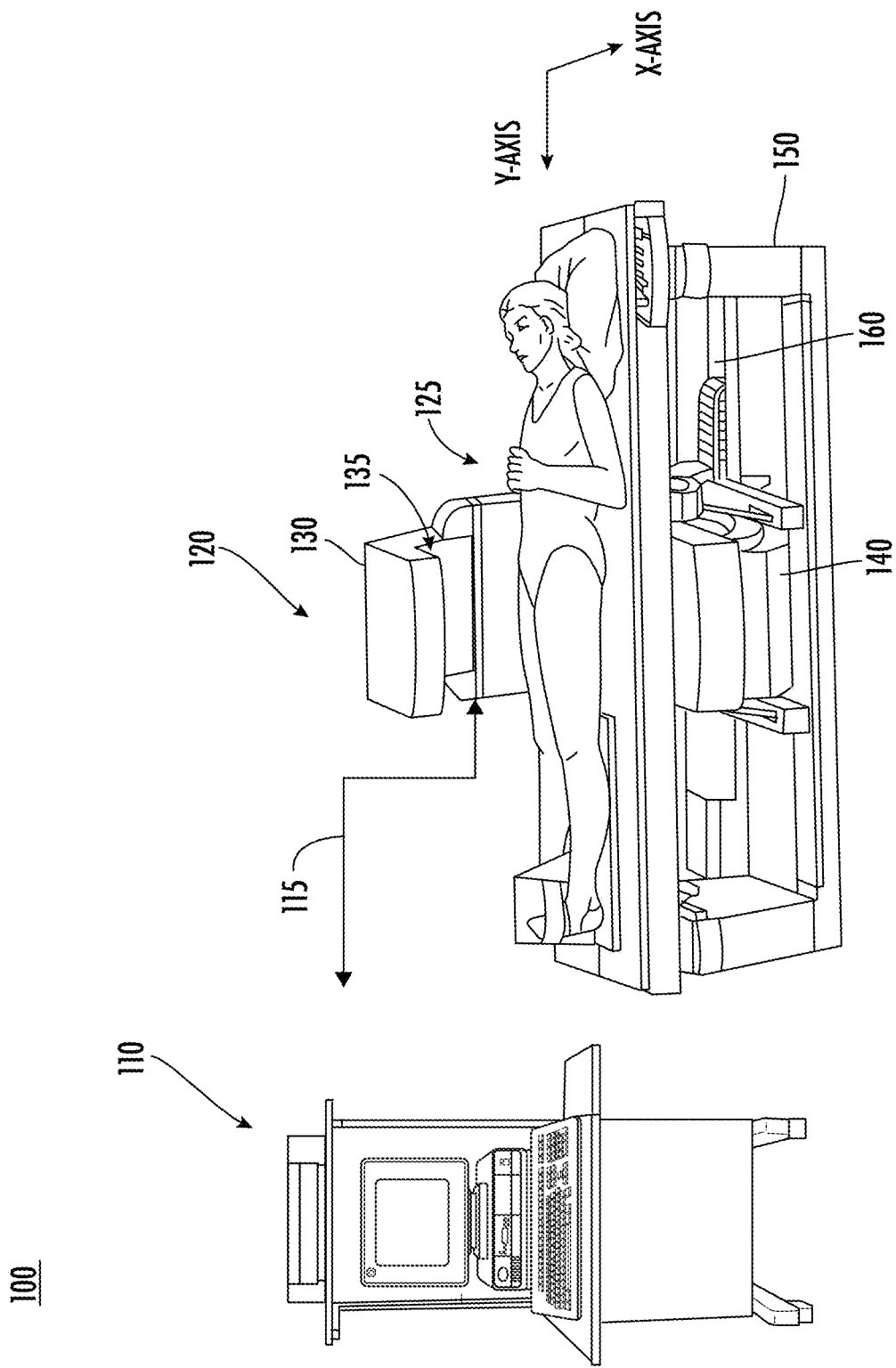
FIG. 1 illustrates an exemplary embodiment of a continuous calibration dual-energy X-ray absorptiometry ("DXA") system designed according to principals disclosed herein.

A continuously calibrating, dual-energy X-ray absorptiometry ("DXA") system is described that comprises an x-ray source and detector pair configured to move during a DXA scan in a scan path along the body, where the scan path includes an active scan portion and one or more reference measurement portions. During the active scan portion of the scan path, x-ray energy emitted by the x-ray source and attenuated by the patient is recorded by the x-ray detectors and forwarded to image processing software to generate a DXA scan image. During the one or more reference measurement portions of the scan path, a calibration element formed of a reference material having known x-ray attenuation properties is positioned between the x-ray source and x-ray detector, and the x-ray energies emitted by the x-ray source and attenuated by the calibration element are captured as one or more reference measurements for Quality Control (QC) purposes.

In one embodiment, at least one reference measurement portion is positioned at a location within the scan path that is aligned with a low attenuation patient feature, such as a patient's soft tissue mass or a patient boundary. Selecting reference measurement locations within the scan path that are aligned with low attenuation patient features helps to mitigate the influence of patient x-ray attenuation on the QC reference measurement to improve QC reference measurement accuracy.

In some embodiments a reference measurement location is selected based on its position relative to an active scan area, wherein the active scan area refers to the area from which scan data is collected during a patient scan, and a reference measurement location may be any accessible scan data location at the edge of or outside of the active scan area.

According to one aspect, the one or more reference measurements may be compared against an expected x-ray absorptiometry profile for the calibration element to identify variances that are indicative of DXA system performance issues. If the variances indicate performance issues, the DXA system may trigger corrective actions, including one or more of adjusting scan data recorded by the scan to normalize the variances, initiating a QC calibration process, adjusting scan data prompting for a new DXA scan, adjusting scan data for subsequently recorded DXA scans, and the like.

Such an arrangement provides a high confidence, high utilization, lower dose DXA solution for determining fracture risk during the assessment and management of osteoporosis. High confidence is obtained by enabling real time DXA scan correction as described above. By using reference measurement locations in the scan path that are at the edge of or outside the active scan area, heretofore unused DXA scan time can be used for quality control purposes, thereby increasing DXA system utilization.

Embodiments of the continuously calibrating DXA system disclosed herein improve upon prior art calibration arrangements by providing a technique to continuously adjust DXA scan data to compensate for drifts in system performance caused by changing temperatures, processing loads, etc. over time.

One prior art system capable of continuously calibrating DXA scan data is disclosed in U.S. Pat. No. 4,947,414, entitled Bone Densitometer and issued August 1990 to Jay A. Stein of Hologic, Inc. (hereinafter the "414 patent"). The '414 patent Abstract discloses a DXA system comprising a dual-voltage pencil beam x-ray source directed towards an integrating detector timed to integrate a detected signal of a patient-attenuated pencil beam over each x-ray pulse. The integrated signals are converted to digital values representing a bone density of the patient.

The '414 patent describes a calibration mechanism having a calibration disc including a material having x-ray attenuation characteristics similar to bone, mounted such that a region of the disc near the circumference including the material interrupts the pencil beam as the disc rotates. The calibration disc is synchronized to the switching frequency of the high voltage power supply and divided into four quadrants (two bone, two non-bone). Four measurements are collected by the main detector at each imaging location, including high energy and low energy measurements for both bone and non-bone disc quadrants, with the separation between the high and low energy values providing a calibration constant to the bone mineral content.

In contrast to the '414 patent system, which performs multiple readings at each imaging location for calibration purposes, the continuous calibration DXA system disclosed herein adds no extra time to a DXA scan, but rather takes advantage of heretofore unused DXA scan time to continuously collect QC reference measurements that may be used to address DXA scan issues in real-time.

FIG. 1 illustrates several exemplary components that may be included in a continuously calibrated DXA system 100. The DXA system 100 is shown to include a workstation 110 communicatively coupled by network 115 to a DXA scanner 120. In one embodiment, the workstation may comprise any network-enabled computer comprising or capable of accessing a memory and a processor. Image processing software may be stored in the memory of the workstation and may be operable when executed upon by the processor to process image data received from the DXA scanner 120 to obtain information such as BMD, BMC and/or other body composition information interpretable from a DXA scan. The image processing software may use various algorithms for interpreting the image data, such as those included in the APEX® 2.0 or Delphi® software provided by Hologic, Inc., of Marlboro Massachusetts, U.S.A., the Lunar Prodigy® software provided by General Electric Healthcare, Inc. of Madison, WI, USA.

Network 115 may be one or more of a wireless network, a wired network or any combination of wireless network and wired network configured to connect the DXA scanner 120 to workstation 110. Network 115 may include one or more of a fiber optics network, a passive optical network, a cable network, a cellular network, an Internet network, a satellite network, a wireless local area network (LAN), a Global System for Mobile Communication ("GSM"), a Personal Communication Service ("PCS"), a Personal Area Network ("PAN"), Wireless Application Protocol (WAP), Multimedia Messaging Service (MMS), Enhanced Messaging Service (EMS), Short Message Service (SMS), Time Division Multiplexing (TDM) based systems, Code Division Multiple Access (CDMA) based systems, D-AMPS, Wi-Fi, Fixed Wireless Data, IEEE 802.11b, 802.15.1, 802.11n and 802.11g, Bluetooth, Near Field Communication (NFC), Radio Frequency Identification (RFID), Wi-Fi, and/or the like. Network 115 may further include one network, or any number of the exemplary types of networks mentioned above, operating as a stand-alone network or in cooperation with each other.

The DXA scanner 120 in one embodiment is configured as a continuously calibrated DXA scanner disclosed herein. The DXA scanner 120 is shown to include a support structure 130 moveably coupled to a patient support table 150. An x-ray source assembly 140, coupled to the support structure 130, is positioned below patient support table 150. An x-ray detector assembly 135, also coupled to the support structure 130, is positioned above the patient support table 150 such that x-rays emitted from an x-ray source of the x-ray source assembly 140 are directed towards an x-ray detector of the x-ray detector assembly 135. During a DXA scan of a patient 125, in one embodiment as the support structure 130 is moved in the y-axis along a rail 160 of the patient support table, the x-ray source assembly 140 and the x-ray detector assembly 135 synchronously move the respective x-ray source and x-ray detector back and forth along the x-axis to collect scan data.

Figure 2:
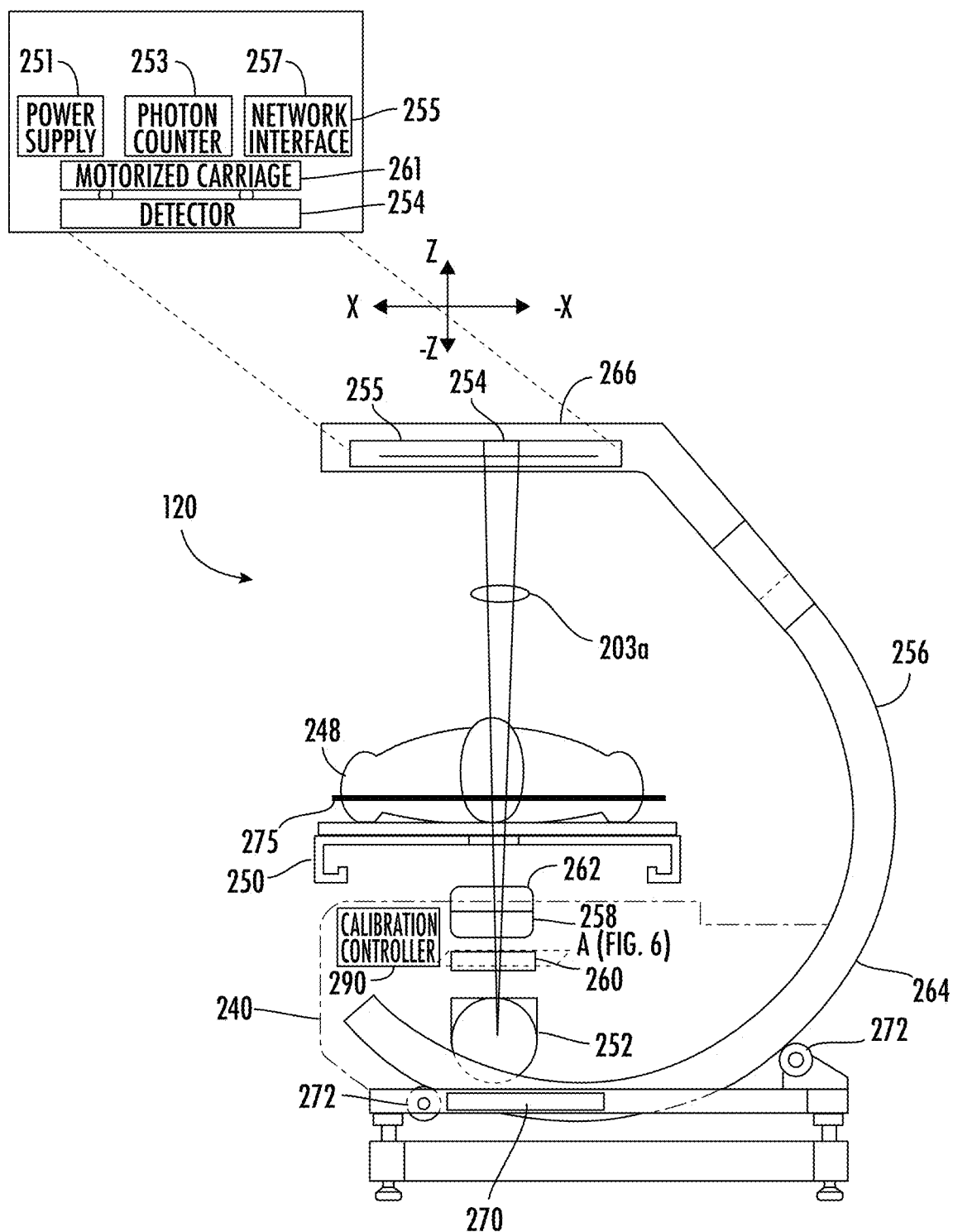
FIG. 2 is a cross section of the continuous calibration DXA system of FIG. 1.

FIG. 2 is a more detailed diagram of the DXA scanner 120, illustrating a patient 248 lying upon patient support table 250. X-rays from an X-ray source 252 located beneath patient support table 250 pass through patient 248 and are received by a detector 254 having an array of detector elements located above the patient 248.

Both an X-ray source assembly 240 and an x-ray detector assembly 255 are supported by C-arm 256 which maintains a selected source-to-detector distance and alignment. C-arm 256 includes a central portion 264 which can be combined with the x-ray source assembly 240. In one embodiment, the C-arm may advantageously house a motorized carriage 270 for moving the x-ray source assembly 240 back and forth along the X-axis during a scan. As described in FIG. 1, the C-arm may also comprise motorized control that enables it to move along the Y-axis during a scan. Movement of the C-arm may be automatic during the scan or may be controlled via an operator control panel mounted on the C-arm or via the workstation 110.

According to one embodiment, the x-ray source and detector assemblies are arranged as a narrow angle fan beam x-ray system, where the x-ray beams are narrowly collimated towards the detector array, the x-ray source and x-ray detector move together along the scan path, and the x-ray detector captures and forwards patient attenuated DXA scan data as it moves through the active scan area. Narrow angle fan beam and pencil beam x-ray systems, which include smaller detectors, are generally lower cost alternatives to fan beam DXA scan technologies. It should be noted that, although narrow angle fan beam x-ray systems are disclosed herein, the present invention is not limited to the use of narrow angle fan beam systems but may also include pencil beam systems and other such systems where a detector moves together with the x-ray source during a scan. In addition, it is further envisioned that fan beam systems and cone beam systems may also be configured by those of skill in the art to capture reference measurements from non-active scan areas of a DXA scan for QC use, for example with a flat panel digital detector typically used in general radiography. Accordingly, the techniques disclosed herein are not limited for use with any particular x-ray beam profile system.

X-ray source assembly 240 is shown to include an X-ray source 252, a filter 262, a calibration element 260 and a slit collimator 258. According to one aspect, the x-ray source 252 may include an x-ray controller and x-ray tube. In one embodiment, the x-ray tube is powered using a fixed voltage supply and produces a single energy x-ray beam that is formed, using the filter and slit collimator, into a narrow angle fan beam. An exemplary x-ray source is an X5135 100 kV 1 mA model manufactured by Spellman High Voltage Electronics of Hauppauge, NY The x-ray source 252 may be located in the lower section of the C-arm with the x-ray beam 203a directed upwards through the tabletop to be incident on the x-ray detector 254. In FIG. 2, the x-ray source assembly is shown coupled to a motorized carriage 270 configured to move the x-ray source along the x-axis during a scan, wherein the movement of the x-ray source 252 may be synchronized with the movement of the x-ray detector 254. In one embodiment, movement of the x-ray source assembly 240 may be controlled automatically by the system during scanning and, when scanning is not in progress, via an operator control panel or via input from the workstation 110.

According to one aspect, as illustrated, a filter 262 may be positioned in front of the collimator 258 (e.g., the filter 262 may be positioned between the collimator 258 and the detector). Alternatively, the filter 262 may be positioned between the x-ray source 252 and the collimator 258. The filter 262 is preferably selected to filter out a selected energy range, so that a high and low energy pass therethrough, thereby providing the dual-energy x-ray signal for the DXA scan. For example, a k-edge filter comprising a piece of material containing a rare-earth metal may be positioned in the x-ray beam's path, where the k-edge filter includes electrons in the K band that preferentially absorb x-rays at roughly half the energy of the x-ray source's maximum energy, splitting the x-ray beam into high and low energy lobes for use in DXA imaging. Exemplary materials that may be used as the k-edge filter include cerium and samarium having a thickness of 250μ±150μ (0.250 mm±0.150 mm), although equivalent materials and other thickness values may be substituted herein without affecting the scope of the invention.

In one embodiment the calibration element 260 may comprise a material having attenuation properties similar to bone, for example selected from a group including but not limited to bone, aluminum or a suspension of calcium phosphate compound in epoxy resin. During each reference measurement portion of the DXA scan, each time that the calibration element is moved into the path of the x-ray beam, one or more reference measurements may be collected by each detector of the detector array. Because each detector of the array is exposed to the same calibration element during a reference measurement, variations between detectors within an array may be quickly identified.

The example x-ray source assembly of FIG. 2 is also shown to include a collimator 258. In one embodiment, the collimator may include x-ray shielding material to effectively block all x-ray radiation emitted from the x-ray source 252 except for that which is emitted through the collimator window. The x-ray collimator size and shape in one embodiment may be configured to produce a narrow angle fan beam or other profile x-ray. In some embodiments, the collimator 258, calibration element 260, calibration controller 290 and filter 262 may be provided as part of a collimator assembly. While in the embodiment of FIG. 2, the filter 262 is shown positioned in front of the collimator 258 and the calibration element 260 is shown positioned between the x-ray source 252 and the collimator 258 to reduce scatter, the present invention is not limited to any particular order of elements within the x-ray source assembly.

In one embodiment, an upper arm portion 266 of C-arm 256 may comprise a removable portion that houses X-ray detector assembly 255. In one embodiment, the x-ray detector assembly 255 may comprise a digital x-ray detector 254 comprised of a direct bandgap semiconductor such as a Cadmium Zinc Telluride (CZT) Detector, a power supply 251, a photon counter 253 and a network interface 257. CZT detectors may be fabricated with very thin metalized electrode geometries deposited on the detector surfaces that have been electrically biased to create a difference in electrical potential within the detector volume. When ionizing radiation from the x-ray source interacts with the CZT crystal, a voltage pulse whose height is proportional to the incident energy of the incoming photon is generated and fed to electronics that incorporate a pulse height discriminator or comparator circuit to sort the photons into high and low energy bins, thereby counting photons based on their energy to obtain a characteristic spectrum for the incoming photons. An example of an x-ray detector that may be used herein comprises a CZT model keV-350 x-ray detector manufactured by eV Products, Inc., of Saxonburg, PA, USA.

In one embodiment, the detector 254 comprises an array of elements, such as an array of 64 elements arranged as 2 rows of 32 individual x-ray sensors. The detector 254 is oriented so that the long axis of the detector array is parallel to the long axis of the patient support table 250. As will be described in more detail below, during operation, the detector 254 may be swept back and forth across the patient, capturing multiple DXA scan readings which are forwarded from the detector to image processing circuitry at workstation 110.

In on embodiment, the x-ray detector 254 may be coupled to a motorized carriage 261 located inside the upper section of the C-arm with the active receptors of detector 254 facing downwards toward the X-ray Source. The motorized carriage may be configured for motorized linear motion along the X axis and may be synchronized with the motorized carriage 270 supporting the x-ray source assembly. Detector motion may be controlled automatically by the system during scanning and, when scanning is not in progress, via an operator control panel or via input from the workstation 110.

During a scan operation, in one embodiment C-arm 256 may rotate about a rotational axis which extends along the Y-axis (normal to FIG. 2) and is at the geometric center of portion 264 of C-arm 256. In addition, C-arm 256 may progress on rollers 272 along the Y-axis (i.e., along the length of a patient and thus along the patient's spine). In some embodiments, patient support table 250 may be translatable along all three axes—the longitudinal (Y-axis), the transverse (X-axis), and the vertical (Z-axis). C-arm 256 may be configured to move in conjunction with patient support table 250.

Carried by C-arm 256, x-ray source assembly 240 and x-ray detector assembly 255 thus progress along both the X and Y planes with respect to patient 248 during a scan. Motion in the longitudinal Y direction moves the source/detector pair along the patient axis as defined by the spine, while axial motion rotates the source/detector pair around the patient. The center of rotation is not the focal spot in the X-ray tube, but rather an imaging plane 275, which comprises a plane parallel to and above the patient support table 250. Signals produced by the detector 254 in response to x-rays impinging thereon are collected by the detector and forwarded to the workstation 110 for further image processing. The processor may provide resulting density representations, and/or images, and/or reports of measured and/or calculated parameters, using principles disclosed U.S. Pat. No. 8,634,629, issued Jan. 21, 2014 to Kevin Wilson of Hologic, Inc., and incorporated herein by reference.

Figure 3:
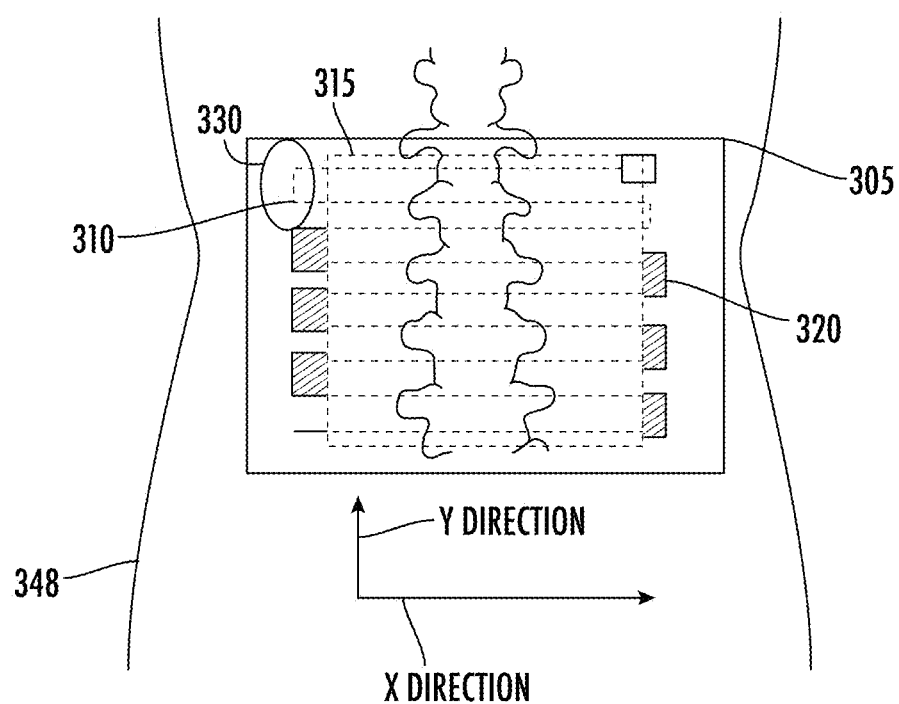
FIG. 3 is a diagram illustrating a scan path of the continuous calibration DXA system of FIGS. 1 and 2.

FIG. 3 is a top-down perspective view 300 of a patient 348, illustrating an exemplary available scan area 305, an active scan area 315 and an exemplary scan path 310 which may be followed by the x-ray source/x-ray detector pair during a DXA scan operation.

According to one aspect, the available scan area 305 comprises that area capable of being traversed by the DXA system during a scan; i.e., the mechanical extent of the x-ray source/x-ray detector's travel. The active scan area 315 includes that area that may produce relevant patient data. In some embodiments, the active scan area 315 may be pre-defined and common for any DXA scan. In other embodiments, the active scan area 315 may vary in accordance with the size and shape of the patient. In any embodiment, the area within the available scan area 305 but outside the active scan area 315 comprises a reference measurement area; i.e., an area across which the x-ray source and x-ray detector may travel without producing productive DXA scan information that can instead be used for collecting QC reference measurements for real-time or near real-time correction of the DXA scan data.

For example, FIG. 3 illustrates an exemplary scan path 310 along which an x-ray source and x-ray detector pair may travel when capturing DXA scan data. In FIG. 3, the scan path 310 is comprised of a boustrophedon or raster-scan path pattern, although the present invention is not limited to any particular scan pattern. The scan path 310 is shown to include a number of reference portions 330, wherein the reference portions 330 may comprise those portions of the scan path 310 that lie outside of the active scan area 315 of the available scan area 305. In FIG. 3, the reference portion 330 is shown to comprise that portion of the scan path 310 where the x-ray source/x-ray detector pair stop travel along a first x-axis, advance along a y-axis, and continue in the other direction along the x-axis, wherein for the purposes of this disclosure such reference portion is referred to as a 'turnaround.'

The time period during which the x-ray source/x-ray detector are within each reference portion 330 of the scan may vary according to DXA system design. In some embodiments, the time period during which patient DXA scan data may be collected may comprise up to 50% or more of the total DXA scan time; thus, for a three minute scan, 90 seconds may be used for patient DXA data collection, while for 90 seconds of the DXA scan time, the x-ray source/detector pair are within the reference measurement area. Changes in motion of the x-ray tube/detector pair during the turnaround may adversely impact DXA scan image quality, and thus have historically been omitted from consideration. The placement of the calibration element proximate to the x-ray source reduces the impact of such motion on reference measurements. As a result, valuable calibration information may be captured during previously unused portions of a DXA scan to increase the quality and confidence in the final DXA scan result in real time. In addition, during time spent in the reference measurement area, one or multiple reference measurements may be collected. Collecting multiple reference measurements during a reference portion(s) 330 of the scan path 310 may help to minimize the impact of random anomalies during reference measurements. In addition, by attenuating x-ray beams during reference measurements, patient dosing is advantageously reduced.

In the example of FIG. 3, each shaded element along the scan path 310 in the reference measurement area, such as shaded element 320, represents an exemplary QC reference measurement location. As shown in FIG. 3 it would be possible, although not necessary, to acquire a QC reference measurement at each turnaround in the scan path 310. The present invention is not limited to any particular number or arrangement of reference measurement locations along the scan path 310, but rather encompasses DXA calibration solutions that utilize QC reference measurements obtained anywhere along the scan path 310 in the reference measurement area.

Figure 3A:
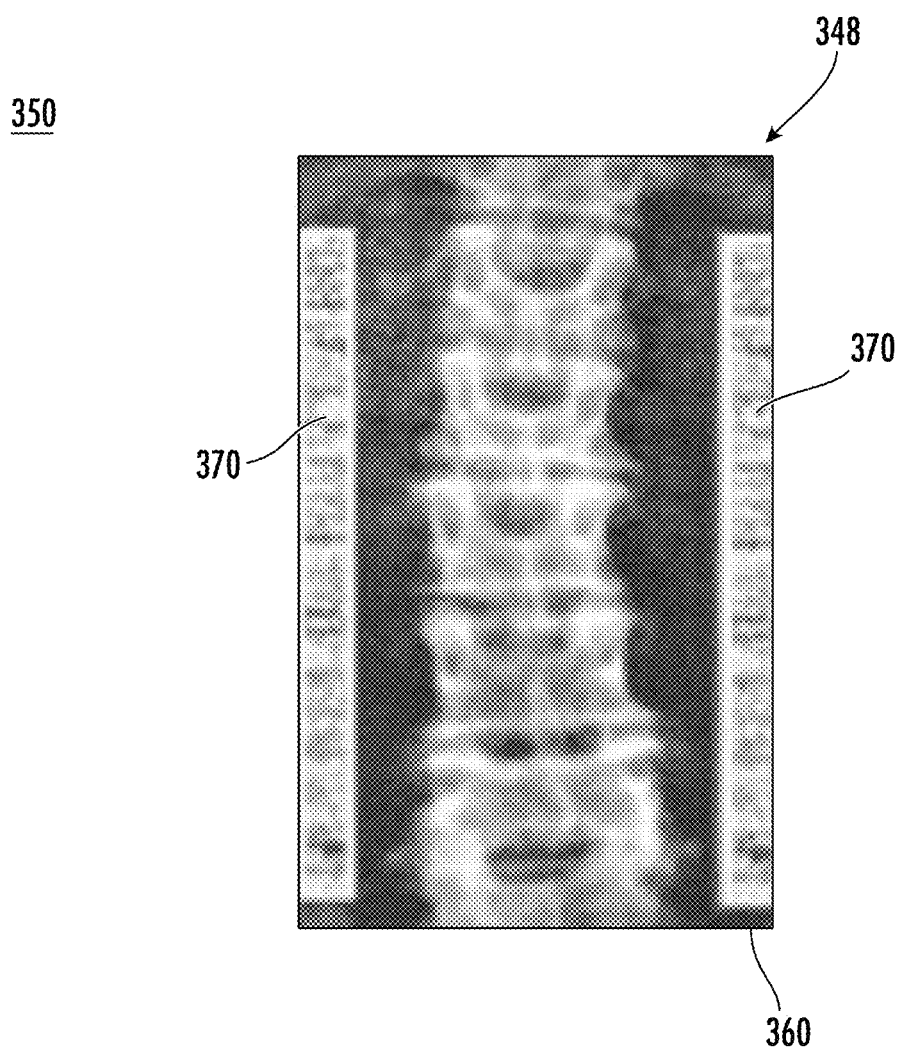
FIG. 3A is an alternate diagram illustrating an image of a continuous calibration DXA system.

FIG. 3A is an alternate top-down perspective view 350 of a patient 348, illustrating an exemplary field of view 360 in accordance with an alternate embodiment of the present disclosure. In accordance with the embodiment of FIG. 3A, the field of view is substantially similar to that described above in connection with FIG. 3, however in accordance with FIG. 3A, the scanning motion along the scan path is eliminated. That is, in accordance with FIG. 3A, there is no scanning motion rather the entire field of view 360 is exposed. In this embodiment, the detector may be, for example, a flat panel detector (e.g., like the detectors used in general radiography). In use, the flat panel detector may be arranged and configured to measure bone mineral density. In this embodiment, one or more calibration elements 370 may be placed in the periphery of the field of view 360 (but within the field of view 360) to provide real time calibration and/or quality control of the measurement. For example, as illustrated, the one or more calibration elements 370 may be placed on either side of the periphery of the field of view 360. In use, the calibration element 370 may be any suitable material now known or hereafter developed such as, for example, a strip of aluminum or a mask that follows the approximate contours of the soft tissue in the periphery of the field of view.

Thus arranged, the desired field of view 360 may be measured in a single exposure or alternating high and low energy exposures but without scanning motion, using an area of the detector (e.g., a digital flat panel detector as in general radiography). In use, the calibration element 370 may be placed in the periphery of the field of view 360, outside of the bony region of interest, e.g. as a linear strip or mask of calibration material conforming to the soft tissue region at the periphery of the bone region under interrogation. The signal from the calibration element 370 is compared to previously determined threshold values; if it is outside a specified range the exam is flagged for corrective action including one or more of a scan modification action and a system adjustment or calibration action.

Figure 4:
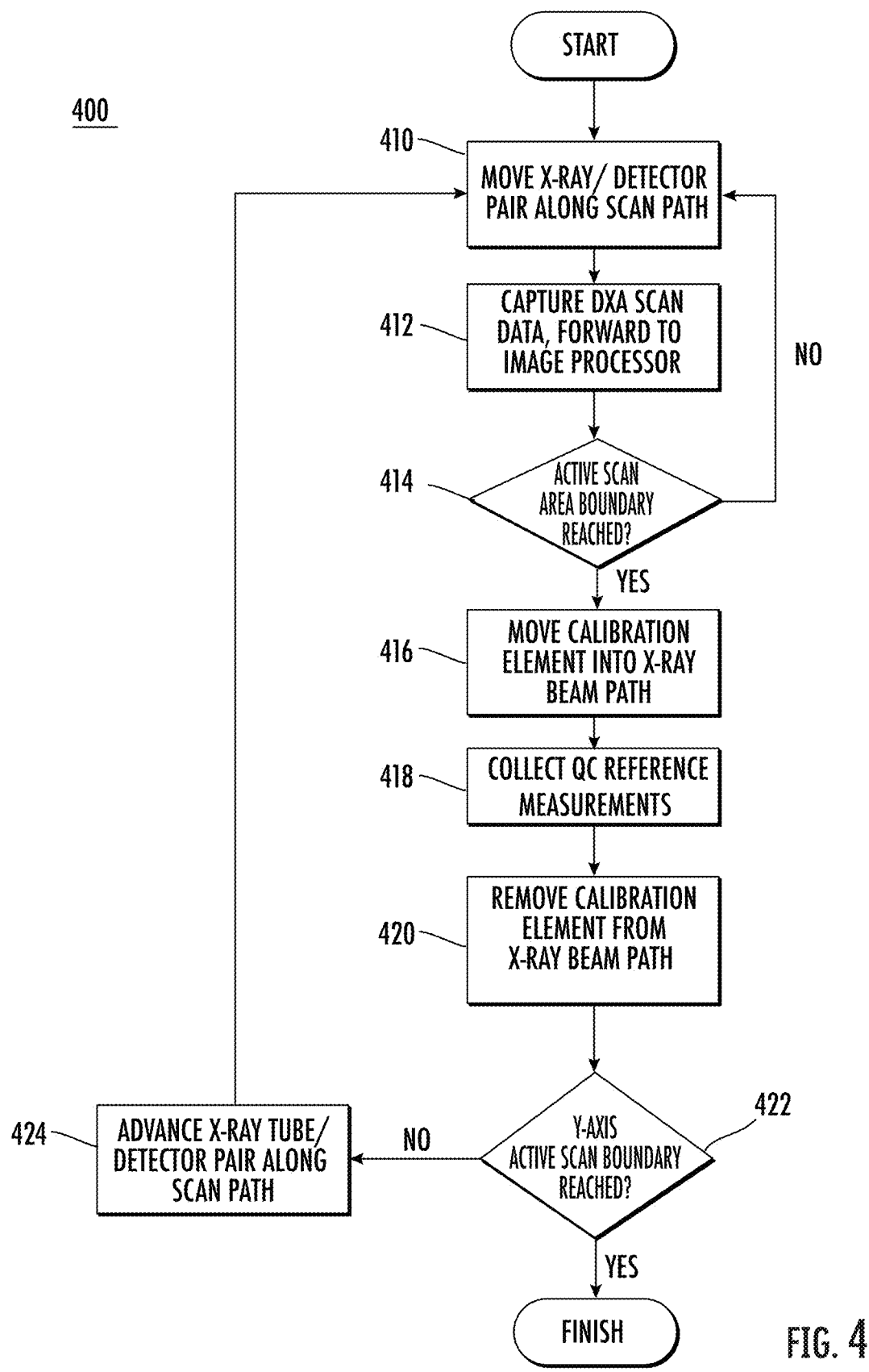
FIG. 4 is a flow diagram illustrating exemplary steps that may be performed during capture of quality control reference measurements in the DXA system of FIG. 1.

FIG. 4 is a flow diagram illustrating exemplary steps that may be performed during a continuous calibration DXA scan process 400 using techniques disclosed herein. Prior to performing the scan, a patient may be positioned on a support table and an active scan area may be defined for the patient, where the active scan area refers to an area from which data will be collected during a patient scan. In some embodiments this area may be calculated by the workstation based on scan parameters and a starting position entered by the scan operator. At step 410 the scan begins with movement of the x-ray source assembly along the x-axis in a first direction by motorized carriage 270. At step 412, while the x-ray source assembly is traversing the x-axis the x-ray detector periodically captures and processes received x-ray energies, translating the energies into pixel intensity values that may be forwarded to image processing software at the workstation.

At 414, when it has been determined that the x-axis active scan area boundary has been reached, C-arm motor may move the x-ray source and detector in unison along the y-axis to the next scan line to enable capture of additional scan data in the next scan line. During this turnaround time (i.e., a reference measurement portion of the scan line) the x-ray tube/detector pair are outside the active scan area 315. At step 416 the calibration element may be moved between the x-ray source and x-ray detector. During the reference measurement the x-ray tube continues to emit radiation that is attenuated by the calibration element and captured by the detector as QC reference measurement(s) at step 418. Following turnaround, at step 420 the calibration element is removed from the x-ray beam path to permit collection of patient scan data.

At step 422 it is determined whether the Y-axis active scan area boundary has been reached, indicating that the DXA scan is complete. If not, then at step 424 the C-arm (and supported x-ray source/detector pair) continues to advance along the scan path. Steps 410-422 are repeated until all scan lines within the active scan area are captured. In some embodiments, the number of active scan lines may comprise, for example, 16 scan lines to capture DXA scan data in an active scan area of 114 mm×152 mm although it can be appreciated that the principles disclosed herein may be used with DXA systems having various scan areas and scan paths, and the present invention is not limited to any particular scan architecture.

Figure 5:
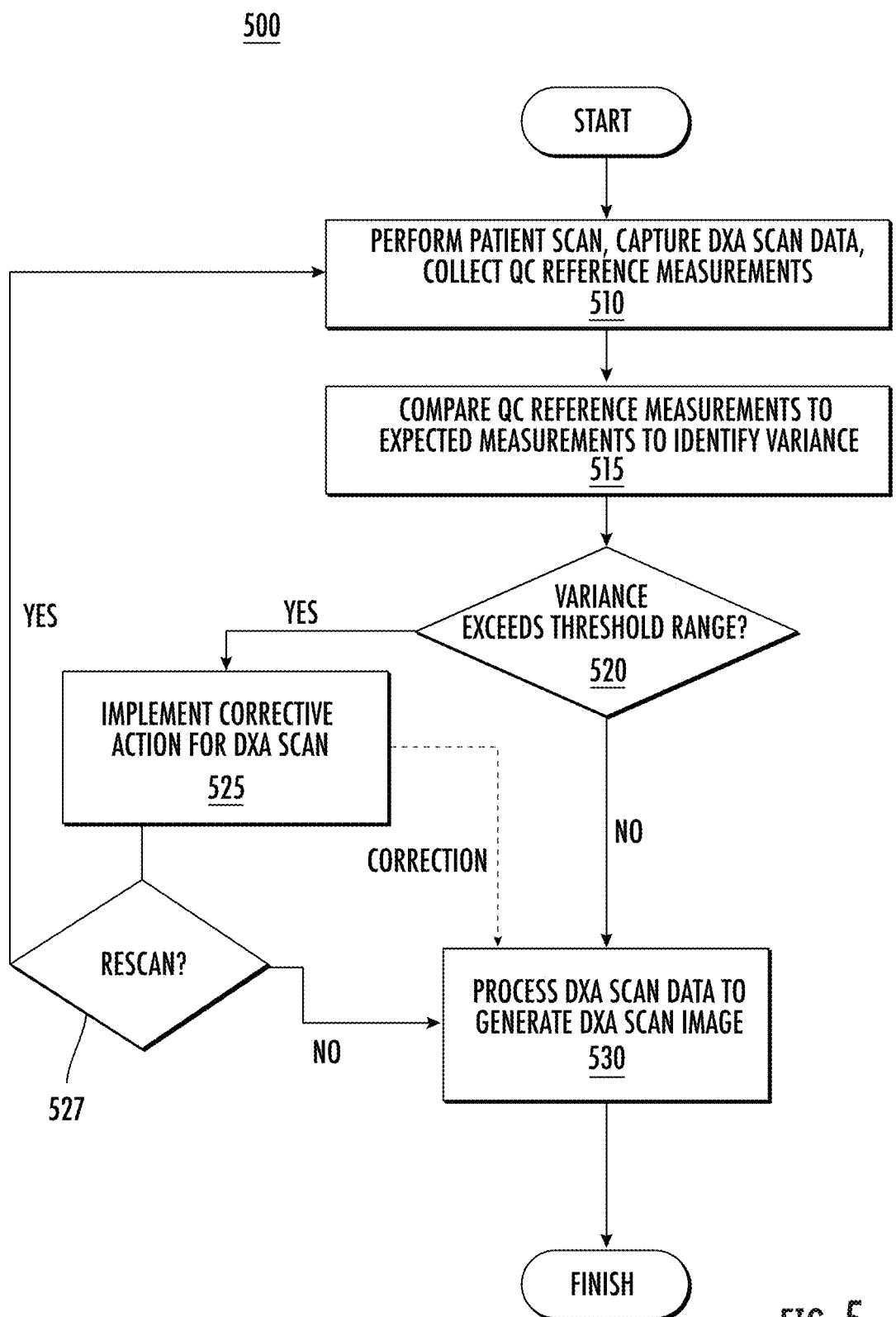
FIG. 5 is a flow diagram illustrating exemplary steps that may be performed to calibrate DXA scans using reference measurements captured using the method disclosed in FIG. 4.

FIG. 5 is a flow diagram illustrating exemplary steps of a process 500 that may be performed for continuous calibration of DXA results using the principals described herein. At step 510 a patient scan is performed as described with regards to FIG. 4, producing DXA scan data as well as QC reference measurements. In one embodiment, the DXA scan data may comprise an array of values, each value representing an intensity of received x-ray energy at a pixel location within the imaging plane. In one embodiment, the imaging plane may be, for example, a plane parallel to and above the patient support table to enable imaging of patient bone and tissue.

As mentioned above, at step 515 the QC reference measurements (i.e. attenuated signal values received by the detectors when the calibration element is disposed between the source and detector) may be compared to an expected calibration measurement to identify a variance between the two. According to one aspect, at step 520 the variance is compared against a threshold range value, and if the variance exceeds the threshold range, at step 525 corrective action may be triggered to adjust the acquired DXA scan. In some embodiments the type of corrective action taken to address the variance may relate to a degree of the variance from the threshold range. Correction actions may include scan modification type corrective actions and system adjustment type actions. Scan modification type corrective actions may include, but are not limited to, updating the DXA scan, for example by adjusting the recorded DXA scan values by an amount to normalize the variation, or by performing a calibration of the DXA system using a phantom or other method and acquiring a new DXA scan for the patient subsequent to such calibration.

In some embodiment, depending upon various considerations such as the degree of variation, following the corrective action, it may be determined at step 527 whether to simply re-process the previous image data (i.e., to adjust individual data values for faulty detectors, etc.), or to re-scan the patient. For image processing, correction information may be forwarded from the corrective action step 525 for image processing at step 530, enabling DXA scan correction in real time. If it is determined at step 527 that a scan should be re-executed, the process returns to step 510 to rescan the patient.

In other embodiments, if the variance from the threshold range is extreme (more than double), and/or more than a predetermined percentage of the reference measurements display variances outside the threshold range, or other predetermined criteria, system adjustment type corrective actions may be taken, actions such as system shutdown, system restart, field service calls and the like. Such system adjustment actions may be operator controlled and/or may execute automatically.

In some embodiments, the expected calibration measurement may be represented as a guard-band, having an upper and lower threshold to account for de minimis signal artifacts. In other embodiments, corrective action may be taken whenever there is any variance from the expected reference measurement although, as mentioned above, the corrective action may differ depending upon the degree of variation.

In some embodiments, multiple QC reference measurements may be collected during a DXA scan, and the process includes considering the entire set of QC reference measurements when determining whether to perform a corrective action. Making decisions based on the entire set of QC reference measurements helps to ensure that reference measurement anomalies do not result in abandonment of otherwise valid DXA scan data and serves to highlight trending performance degradations that may benefit from immediate remediation.

According to one aspect, the process of determining whether corrective action is warranted may include foregoing corrective remedies when a predetermined percentage of QC reference measurements have variances below the threshold range. For example, in a system that captures twenty reference measurements during a scan, corrective action may be averted once five, ten or more of the QC reference measurements are determined to be accurate, as the accurate measurements establish the overall integrity of the DXA system. The particular percentage is a matter of design choice and may vary based on a number of considerations including corrective action history, degree of variances for reference measurements above the threshold range, etc. With such an arrangement, further performance advantages may be gained by effectively 'passing' a DXA scan once the system has been shown to be reliable via a minimum number of accurate reference measurements.

In addition, in embodiments where the corrective action includes adjusting DXA scan values to normalize the variance, the amount to adjust the scan values may be determined in response to the set of one or more of the QC reference measurements obtained during the scan, for example by determining the median or mean of the reference measurements. When determining the appropriate adjustment, for example when calculating the median or mean, certain reference measurements having variances which are above or below threshold ranges may be discarded; for example, QC reference measurements that are captured proximate to a rib or to a femoral bone or open air may skew results and thus may advantageously be discarded.

Calibration of x-ray scan data may be performed retrospectively, prospectively, dynamically, or some combination thereof. For example, adjustments may be added to the current scan data identified as having a variance requiring adjustment and may alternatively be retrospectively and/or prospectively added to previous DXA scan data. For example, if a trending analysis of QC reference measurements exposes a trending performance drift it may be beneficial to retrospectively adjust the DXA scan data exhibiting the trend. Prospective adjustments may be made to DXA scan data for those variances subsequent scans to normalize scan results. With such an arrangement, scan data may be continuously calibrated to account for drifts in system performance caused by system wear and tear and environmental factors, thereby providing a continuously calibrating DXA imaging system with high precision.

Figure 6:
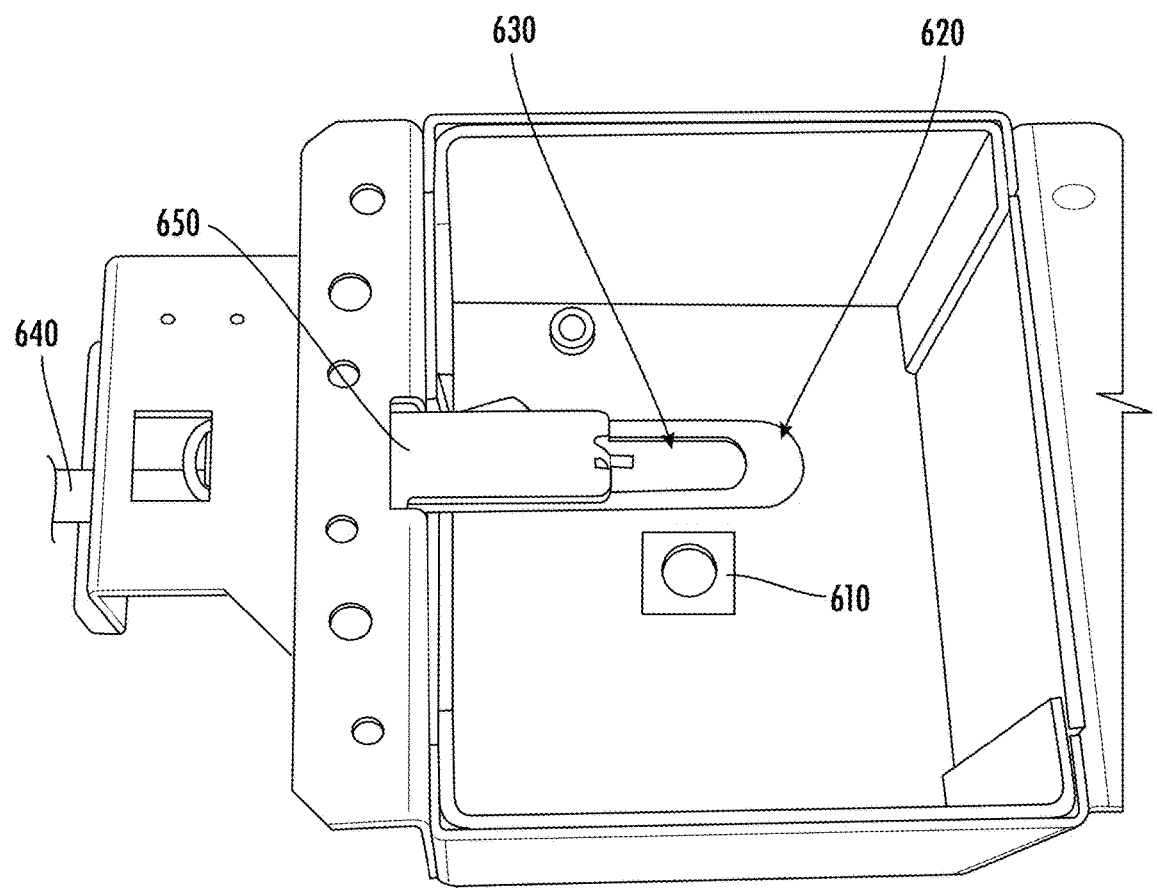
FIG. 6 is bottom-up perspective view of x-ray source assembly components taken along plane A of FIG. 2.

It is appreciated that many mechanisms may be provided by one of skill in the art to move the calibration element into and out of the x-ray beam path to acquire a reference measurement. An exemplary implementation is shown in FIG. 6, which is a bottom-up cross-section perspective of an example x-ray source housing 600 taken along plane A in FIG. 2. X-ray components illustrated in FIG. 6 include a collimator 610, an attenuator 620 defining a pass through 630. During operation, x-ray beams are directed along an x-ray beam path from an x-ray source (not shown) through the pass through 630 towards the collimator 610. According to one aspect a calibration element 650, here shown slidably disposed on the attenuator, may be inserted and removed from the x-ray beam path by solenoid plunger 640 during reference measurement portions of the scan.

Figure 7A:
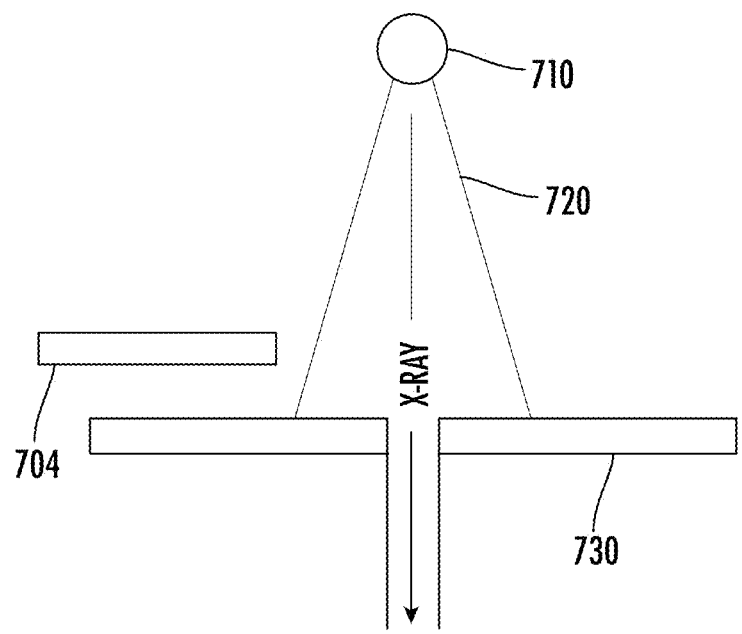
FIG. 7A and FIG. 7B illustrate positioning of the calibration element of FIG. 6 during DXA scans implemented using methods disclosed herein.

FIG. 7A, for example, illustrates a side perspective of an x-ray source 710 emitting an x-ray beam 720 towards a collimator 730. A calibration element 704 (such as element 650 of FIG. 6) may be positioned in an 'out' position relative to the x-ray beam path during an active scan portion of a DXA scan. During a reference measurement portion of the DXA scan, as shown in FIG. 7B, the calibration element is moved into the x-ray beam path and an attenuated version of the x-ray is directed towards the detector and collected as a reference measurement.

Figure 7B:
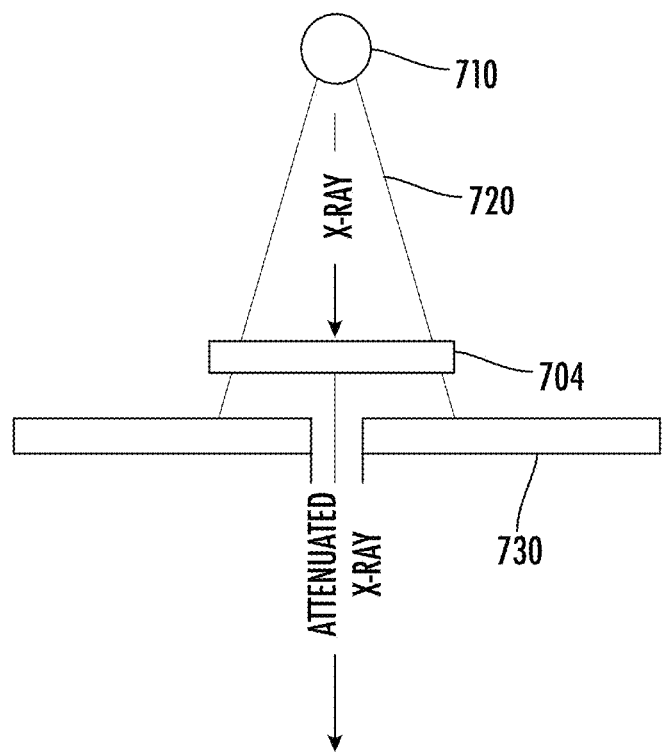

Although a slidable calibration element has been described with regard to FIG. 6 and FIGS. 7A, 7B, it is appreciated that there are many methods for advancing a calibration element into and out of an x-ray beam path, including sliding, rotating, flipping etc., and the present invention is not limited to any particular method of advancement.

Thus, a high precision, high utilization, low dose DXA solution for determining fracture risk during the assessment and management of osteoporosis has been disclosed. High precision is obtained by enabling real time DXA scan correction as described above, and high utilization is achieved by leveraging previously unused DXA scan time for quality control purposes.

Some embodiments may have been described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

As used herein, unless specifically indicated otherwise, the word "or" is used in the inclusive sense of "and/or" and not the exclusive sense of "either/or." Any issued U.S. Patents, allowed applications, published foreign applications, and references that are cited herein are hereby incorporated by reference to the same extent as if each was specifically and individually indicated to be incorporated by reference.

The terms "system," "component" and "unit" are intended to refer to a computer-related entity, either hardware, a combination of hardware and software, software, or software in execution, examples of which are described herein. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Components may be communicatively coupled to each other by various types of communications media to coordinate operations.

With general reference to notations and nomenclature used herein, the detailed descriptions herein may be presented in terms of functional blocks or units that might be implemented as program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but still co-operate or interact with each other.

Various embodiments also relate to apparatus or systems for performing these operations. This apparatus may be specially constructed for the required purpose or it may comprise a general-purpose computer as selectively activated or reconfigured by a computer program stored in the computer. The procedures presented herein are not inherently related to a particular computer or other apparatus. Various general-purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single embodiment to streamline the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodology, but one of ordinary skill in the art may recognize that many further combinations and permutations are possible. Accordingly, the novel architecture is intended to embrace all such alterations, modifications and variations that fall within the spirit and scope of the appended claims.

The invention claimed is:

1. An x-ray system comprising:
   an x-ray source assembly comprising a source carriage configured to move the x-ray source assembly along a scan path during a scan of the x-ray system, the scan path comprising an active scan portion and a reference measurement portion;
   an x-ray detector assembly including a detector carriage configured to move the x-ray detector assembly synchronously with the x-ray source assembly along the scan path and along a longitudinal patient axis substantially perpendicular to the scan path, and to collect scan data at active scan portions of the scan path, wherein the reference measurement portion is laterally outside of the active scan portion along the longitudinal patient axis;
   a support structure including a first end supporting the x-ray source assembly and a second end supporting the x-ray detector assembly;
   a calibration element comprising a material having a known x-ray attenuation value;
   a calibration controller coupled to the calibration element and configured to position the calibration element between the x-ray source assembly and the x-ray detector assembly during the reference measurement portion of the scan path and to remove the calibration element from between the x-ray source assembly and the x-ray detector assembly during the active scan portion of the scan path; and
   a processing unit operable to compare the reference measurement against an expected reference value to identify a variance and to selectively trigger an action in response to the variance.

2. The x-ray system of claim 1 wherein the active scan portion of the scan path comprises scan path locations that are aligned with an active scan area of the x-ray system.

3. The x-ray system of claim 2 comprising an available scan area corresponding to a mechanical extent of travel of the x-ray source and x-ray detector, and wherein the reference measurement portion of the scan path includes at least one scan path location that is within the available scan area but outside the active scan area.

4. The system of claim 3 wherein the reference measurement portion comprises a plurality of reference measurement locations within the scan path that are within the available scan area but outside the active scan area.

5. The x-ray system of claim 3 wherein at least one reference measurement location in the reference portion of the scan path is associated with a scan path location that is aligned with a low attenuation patient feature.

6. The x-ray system of claim 5, wherein the low attenuation patient feature includes one or more of a patient soft tissue mass and a patient boundary.

7. The x-ray system of claim 1 wherein selective triggering of the action occurs in response to the variance exceeding a predetermined threshold range.

8. The x-ray system of claim 7 wherein a type of action is determined according to a degree by which the variance exceeds the predetermined threshold range.

9. The x-ray system of claim 7 wherein selective triggering of action is forestalled if a predetermined percentage of a plurality of reference measurements obtained during the reference portion of the scan path are below the predetermined threshold range.

10. The x-ray system of claim 9 wherein the action includes one or more of a scan modification action and a system adjustment action.

11. The x-ray system of claim 10 wherein the scan modification action includes an adjustment of the scan data by an amount to normalize the variance using a plurality of variances associated with the plurality of reference measurements.

12. The x-ray system of claim 11 wherein the amount is determined based on one of a mean or a median of the plurality of variances.

13. The x-ray system of claim 12 wherein the action applies the amount to retrospective and prospective scan data.

14. The x-ray system of claim 10 wherein the scan modification action includes performing a new scan to produce updated scan data.

15. The x-ray system of claim 10 wherein the system modification action includes system shutdown, system restart and field service notification.

16. The x-ray system of claim 1, wherein the calibration element is comprised of a bone equivalent material.

17. The x-ray system of claim 16 wherein the bone equivalent material comprises one or more of bone, aluminum and calcium phosphate compound.

18. The x-ray system of claim 1 wherein the calibration controller comprises an advancement mechanism for moving the calibration element into an x-ray beam path between the x-ray source and x-ray detector during the reference measurement portion of the scan path.

19. The x-ray system of claim 18 wherein the advancement mechanism comprises a solenoid plunger.

20. The x-ray system of claim 18 wherein the advancement mechanism slides the calibration element into the x-ray beam path.

21. The x-ray system of claim 18 wherein the advancement mechanism rotates the calibration element into the x-ray beam path.

22. The x-ray system of claim 1 wherein the x-ray source emits an x-ray beam having a profile comprising one of a pencil beam, a thin fan beam, a narrow angle fan beam, a wide-angle fan beam, or a cone beam.

23. The x-ray system of claim 22 wherein the x-ray source assembly further includes a filter, positioned in front of a collimator, the filter comprising a rare-earth x-ray filtration material.

24. The x-ray system of claim 1 wherein the scan path is a boustrophedon pattern.

* * * * *